United States Patent
Won et al.

(10) Patent No.: US 8,439,923 B2
(45) Date of Patent: May 14, 2013

(54) POLY-AXIAL PEDICLE SCREW ASSEMBLY

(75) Inventors: Douglas Won, Dallas, TX (US); David Janice, Austin, TX (US)

(73) Assignee: Omni Surgical LLC, Austin, TX (US)

( * ) Notice: Subject to any disclaimer, the term of this patent is extended or adjusted under 35 U.S.C. 154(b) by 590 days.

(21) Appl. No.: 12/661,253

(22) Filed: Mar. 12, 2010

(65) Prior Publication Data

US 2010/0174325 A1 Jul. 8, 2010

Related U.S. Application Data

(63) Continuation-in-part of application No. 12/288,184, filed on Oct. 17, 2008, now Pat. No. 8,382,809.

(51) Int. Cl.
*A61B 17/70* (2006.01)

(52) U.S. Cl.
USPC .......................... 606/86 A; 606/306; 606/264

(58) Field of Classification Search .................. 606/246, 606/250–279, 86 A
See application file for complete search history.

(56) References Cited

U.S. PATENT DOCUMENTS

| | | | |
|---|---|---|---|
| 4,763,644 A * | 8/1988 | Webb | 606/267 |
| 6,740,086 B2 | 5/2004 | Richelsoph | |
| 6,740,089 B2 * | 5/2004 | Haider | 606/302 |
| 7,179,261 B2 | 2/2007 | Sicvol | |
| 7,491,218 B2 | 2/2009 | Landry | |
| 7,547,318 B2 | 6/2009 | Birkmeyer | |
| 7,758,617 B2 * | 7/2010 | Iott et al. | 606/246 |
| 7,842,044 B2 * | 11/2010 | Runco et al. | 606/104 |
| 7,846,093 B2 * | 12/2010 | Gorek et al. | 600/206 |
| 7,918,857 B2 * | 4/2011 | Dziedzic et al. | 606/86 A |
| 7,918,858 B2 * | 4/2011 | Stad et al. | 606/86 A |
| 7,922,727 B2 * | 4/2011 | Songer et al. | 606/86 A |
| 7,927,360 B2 * | 4/2011 | Pond et al. | 606/265 |
| 7,931,673 B2 * | 4/2011 | Hestad et al. | 606/246 |
| 7,947,045 B2 * | 5/2011 | Hestad et al. | 606/86 A |
| 7,955,363 B2 * | 6/2011 | Richelsoph | 606/305 |
| 8,002,798 B2 * | 8/2011 | Chin et al. | 606/246 |
| 8,097,026 B2 * | 1/2012 | Gorek | 606/279 |
| 8,202,274 B2 * | 6/2012 | McLean | 606/86 A |
| 8,211,110 B1 * | 7/2012 | Corin et al. | 606/86 A |
| 8,246,659 B2 * | 8/2012 | Vonwiller et al. | 606/279 |
| 8,262,662 B2 * | 9/2012 | Beardsley et al. | 606/86 A |
| 2002/0116006 A1 | 8/2002 | Cohen | |
| 2004/0162560 A1 * | 8/2004 | Raynor et al. | 606/73 |
| 2005/0065517 A1 * | 3/2005 | Chin | 606/61 |
| 2005/0085813 A1 * | 4/2005 | Spitler et al. | 606/61 |
| 2005/0131408 A1 | 6/2005 | Sicvol | |
| 2005/0182410 A1 * | 8/2005 | Jackson | 606/73 |
| 2005/0192570 A1 * | 9/2005 | Jackson | 606/61 |

(Continued)

*Primary Examiner* — Mary Hoffman
(74) *Attorney, Agent, or Firm* — David O. Simmons (57) ABSTRACT

A clamping body for a pedicle screw assembly has an axial passage extending axially between first and second end portions thereof. The spine rod-receiving channel extends through the first end portion in a traverse direction with respect to the axial passage thereby forming upstanding leg portions of the clamping body and closed end portion of the spine rod-receiving channel. A material thickness reducing relief is provided in an outer surface of each one of the upstanding leg portions at a location between the closed end portion of the spine rod receiving channel and the first end portion of the clamping body whereby the a partial segment of the upstanding leg portions are frangibly detachable. A bridge member is frangibly connected between the upstanding leg portions at the first end portion of the clamping body. The bridge member spans across the spine rod-receiving channel.

11 Claims, 4 Drawing Sheets

U.S. PATENT DOCUMENTS

| | | |
|---|---|---|
| 2006/0247658 A1* | 11/2006 | Pond et al. .................... 606/104 |
| 2007/0219554 A1* | 9/2007 | Landry et al. ................... 606/61 |
| 2008/0082103 A1 | 4/2008 | Hutton |
| 2008/0119849 A1 | 5/2008 | Beardsley |
| 2008/0161857 A1 | 7/2008 | Hestad |
| 2008/0228228 A1 | 9/2008 | Hestad |
| 2008/0262318 A1 | 10/2008 | Gorek |
| 2008/0300638 A1 | 12/2008 | Beardsley |

* cited by examiner

POLY-AXIAL PEDICLE SCREW ASSEMBLY

CROSS REFERENCE TO RELATED APPLICATIONS

This patent application is a continuation-in-part application claiming priority from U.S. Non-Provisional patent application Ser. No. 12/288,184, filed Oct. 17, 2008, now U.S. Pat. No. 8,382,809, entitled "Poly-Axial Pedicle Screw Implements And Lock Screw Therefor", having a common assignee herewith and being incorporated herein in its entirety by reference.

FIELD OF THE DISCLOSURE

The disclosures made herein relate generally to pedicle screw assemblies and, more particularly, to clamping body configurations of poly-axial pedicle screw assemblies.

BACKGROUND

The spinal column is a highly complex system of bones (i.e., vertebral bodies) and connective tissues that provides support for the body and protects the delicate spinal cord and nerves. The spinal column includes a series of vertebrae stacked one atop the other, each vertebral body including an inner or central portion of relatively weak cancellous bone and an outer portion of relatively strong cortical bone. Situated between each vertebral body is an intervertebral disc that cushions and dampens compressive forces on the spinal column. A vertebral canal containing the spinal cord and nerves is located within the forward-facing surface of the vertebral bodies.

There are many types of spinal column disorders. Patients that suffer from such disorders typically experience extreme and debilitating pain, as well as diminished nerve function. Examples of such spinal column disorders include, but are not limited to, scoliosis (i.e., abnormal lateral curvature of the spine), kyphosis (i.e., abnormal forward curvature usually in the thoracic portion of the spine), excess lordosis (i.e., abnormal backward curvature usually in the lumbar portion of the spine), spondylolisthesis (forward displacement of one vertebrae over another usually in the lumbar portion or cervical portion of the spine), etc. There are still other types of spinal column disorders caused by physiological abnormalities, disease and/or trauma such as, for example, ruptured or slipped discs, degenerative disc disease, fractured vertebra, and the like.

Multi-segmental spinal fixation is an accepted surgical procedure in the treatment of such spinal column disorders. It involves the use of a series of pedicle screw assemblies and one or more spine rods. The pedicle screw assemblies each include a screw that is threadedly screwed into one of a plurality of adjacent vertebral bodies. A spine rod (contoured or straight) is fixedly secured to a spine rod clamping body of each one of the pedicle screws for fixing two or more adjacent vertebral bodies in a static relative position. In this manner, spinal fixation can be used to alter the alignment of adjacent vertebrae relative to one another so as to change the overall alignment of the spine, to preclude relative movement between adjacent vertebrae, and the like.

Performing spinal fixation using a minimally invasive surgical procedure is desirable and is becoming more commonplace. A minimally invasive surgical procedure is a surgical procedure that is less invasive than open surgery used for the same type of procedure. Minimally invasive surgery is typically performed through several small incisions (e.g., slits, punctures or the like) as opposed to one or more large incisions as is used in open surgery. By performing the surgical procedure through small incisions, the surgeon can safely work on the site being operated on while disturbing only a minimal portion of surrounding tissue, organs, etc. As a result, patients are less likely to develop complications, they are more likely to recover more quickly, and can typically return to normal activities sooner in comparison to open surgery.

Therefore, pedicle screw assembly that is specifically configured for use in a minimally invasive surgical procedure is advantageous, desirable and useful.

SUMMARY OF THE DISCLOSURE

In one embodiment of the present invention, a clamping body for a pedicle screw assembly has a first end portion, a second end portion and an axial passage extend axially between the first and second end portions. Threads are provided adjacent the second end portion on a surface defining the axial passage. A spine rod-receiving channel extends through the first end portion in a traverse direction with respect to the axial passage thereby forming upstanding leg portions of the clamping body and a closed end portion of the spine rod-receiving channel located between the first and second end portions. A material thickness reducing relief is provided in an outer surface of each one of the upstanding leg portions at a location between the closed end portion of the spine rod receiving channel and the first portion of the clamping body such that a segment of each one of the upstanding leg portions extending between the material thickness reducing relief and the first end portion of the clamping body is frangibly detachable from a segment of each one of the upstanding leg portions extending between the material thickness reducing relief and the closed end portion of the spine rod receiving channel. A bridge member is connected between the upstanding leg portions at the first end portion of the clamping body. The bridge member spans across the spine rod-receiving channel.

In another embodiment of the present invention, a clamping body for a pedicle screw assembly has a first end portion, a second end portion, and an axial passage extending axially between the first and second end portions. Threads are provided adjacent the second end portion on a surface defining the axial passage. The spine rod-receiving channel extends through the first end portion in a traverse direction with respect to the axial passage thereby forming upstanding leg portions of the clamping body. A closed end portion of the spine rod-receiving channel is located between the first and second end portions. A material thickness reducing relief is provided in an outer surface of each one of the upstanding leg portions at a location between the closed end portion of the spine rod receiving channel and the first end portion of the clamping body such that a segment of each one of the upstanding leg portions extending between the material thickness reducing relief and the first end portion of the clamping body is frangibly detachable from a segment of each one of the upstanding leg portions extending between the material thickness reducing relief and the closed end portion of the spine rod receiving channel. A bridge member is frangibly connected between the upstanding leg portions at the first end portion of the clamping body. The bridge member spans across the spine rod-receiving channel.

In another embodiment of the present invention, a pedicle screw assembly comprises a cylindrically-shaped clamping body and a screw. The clamping body has a first end portion and a second end portion, an axial passage extending axially between the first and second end portions, a spine rod receiving channel extending through the first end portion in a traverse direction with respect to the axial passage thereby forming upstanding leg portions of the clamping body and a closed end portion of the spine rod receiving channel located between the first and second end portions, threads provided adjacent the first end portion on a surface defining the axial passage, a material thickness reducing relief provided in an outer surface of each one of the upstanding leg portions at a location between the closed end portion of the spine rod receiving channel and the first end portion of the clamping body such that a segment of each one of the upstanding leg portions extending between the material thickness reducing relief and the first end portion of the clamping body is frangibly detachable from a segment of each one of the upstanding leg portions extending between the material thickness reducing relief and the closed end portion of the spine rod receiving channel; and at least one bridge member connected between the upstanding leg portions at the first end portion of The bridge member spans across the spine rod receiving channel. An edge surface of the bridge member defines an end face of the clamping body. The screw includes a shaft and a semi-spherical shaped head attached to an end portion of the shaft. The shaft has bone-engaging threads provided along a length thereof. The screw head is secured within the second end portion of the clamping body in a manner that limits axial displacement of the screw in a direction toward the second end portion of the clamping body, that allows pivoting of the clamping body about said screw head, and that allows rotation of the clamping body about a longitudinal axis thereof.

These and other objects, embodiments, advantages and/or distinctions of the present invention will become readily apparent upon further review of the following specification, associated drawings and appended claims.

DETAILED DESCRIPTION OF THE DRAWING FIGURES

Pedicle screw implements in accordance with embodiments of the present invention (e.g., pedicle screw assemblies, clamping bodies and the like) are used in performing multi-segmental spinal fixation to alter the alignment of adjacent vertebrae relative to one another so as to change the overall alignment of the spine, to preclude relative movement between adjacent vertebrae, and the like. Advantageously, such pedicle screw implements improve the effectiveness of multi-segmental spinal fixation. Specifically, such pedicle screw implements have a construction that enhances functionality associated with readily and rigidly accommodating a spine rod bent to the contour of the spine, with reliably securing the bent spine rod in a fixed position and orientation, with being threadedly engaged with a vertebral body in a manner that provides superior mechanical strength, and being threadedly engaged with a vertebral body in a manner that minimized adverse deformation and/or damage to the vertebral body. Furthermore, pedicle screws configured in accordance with the present invention have an elongated clamping body, thus making them well-suited for minimally-invasive procedures.

Figure 1:
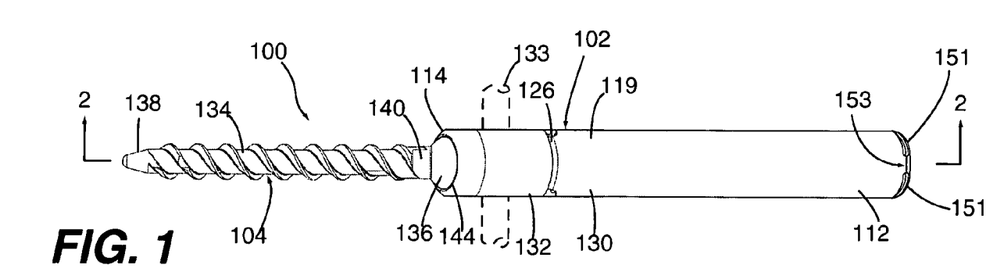
FIG. 1 is a plan view showing a pedicle screw apparatus in accordance with an embodiment of the present invention.
Figure 2:
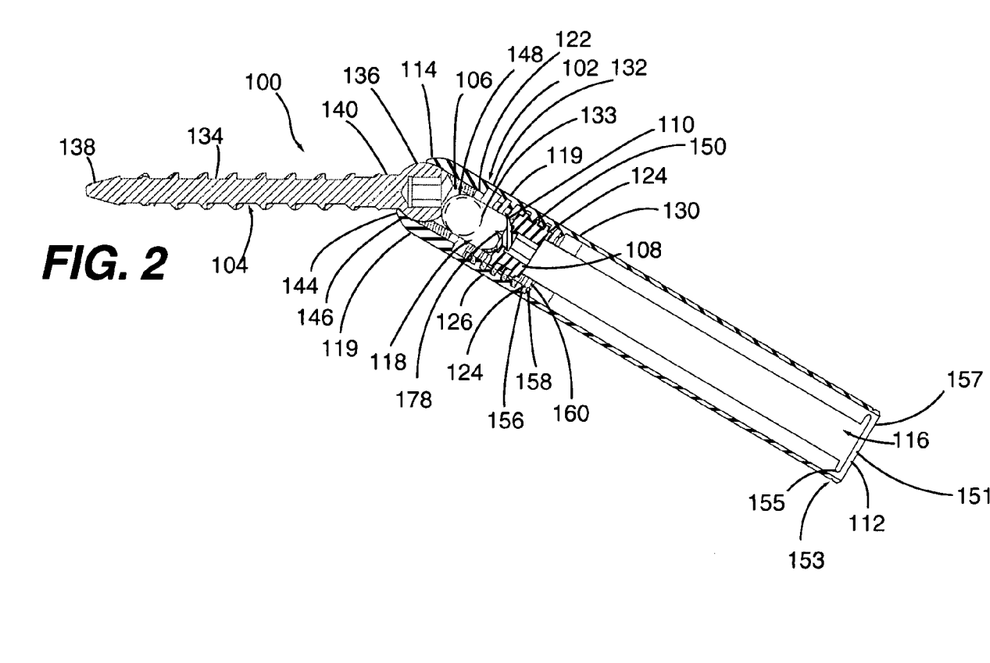
FIG. 2 is a cross sectional view taken along the line 2-2 in FIG. 1.
Figure 3:
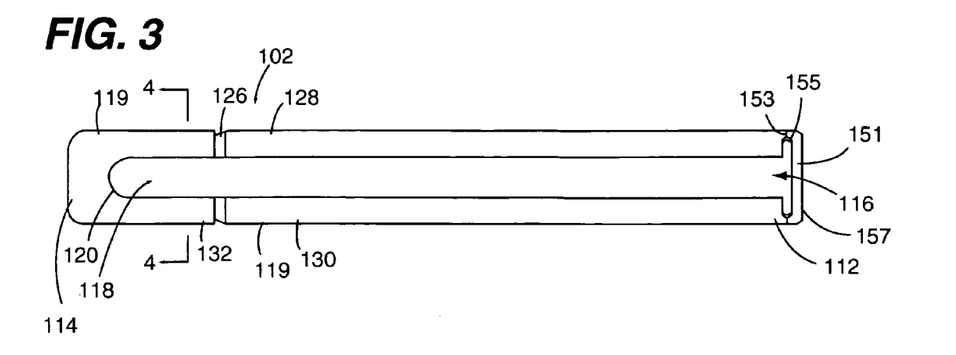
FIG. 3 is a side view of a clamping body for a pedicle screw apparatus in accordance with an embodiment of the present invention.
Figure 4:
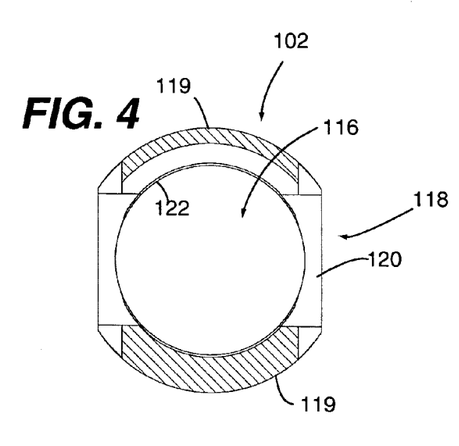
FIG. 4 is a cross sectional view taken along the line 4-4 in FIG. 3.
Figure 5:
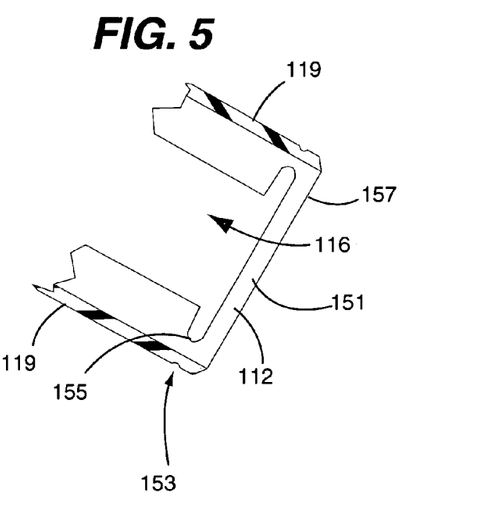
FIG. 5 is a fragmentary view of the cross-sectional view of FIG. 2.

Referring now to FIGS. 1 and 2, a pedicle screw apparatus 100 in accordance with an embodiment of the present invention is shown. The pedicle screw apparatus 100 includes a clamping body 102, a screw 104, a lower saddle 106, a lock screw 108 and an upper saddle 110. As is discussed below in greater detail, the clamping body 102, the screw 104, the lower saddle 106, the lock screw 108 and the upper saddle 110 are constructed and/or interconnected in a manner that provides advantageous functionality and/or structure with respect to known pedicle screw implements.

Referring to FIGS. 1-4, the clamping body 102 has a first end portion 112 and a second end portion 114. An axial passage 116 (shown in FIG. 2) extends axially (i.e., along a longitudinal axis of the clamping body 102) between the first and second end portions 112, 114. A spine rod receiving channel 118 extending through the first end portion 112 in a traverse direction with respect to the axial passage 116, thus forming upstanding leg portions 119 of the clamping body 102. A closed end portion 120 of the spine rod receiving channel 118 is located between the first and second end portions 112, 114. A surface 122 of the clamping body that defines the axial passage 116 has clamping body threads 124 formed therein.

Reliefs 126 (i.e., material thickness reducing reliefs) are provided in an outer surface 128 of the upstanding leg portions 119 of the clamping body 102. In view of the reliefs 126, an upper segment 130 of each upstanding leg portion 119 is frangibly detachable from a lower segment 132 thereof. This frangible functionality provides for ease in engaging and securing a spine rod 133 within the clamping body 102 (i.e., with the upper segments 130 still attached) and for a lower profile of the implanted pedicle screw apparatus 100 (i.e., with the upper segments 130 detached).

Referring to FIGS. 1 and 2, the screw 104 includes a shaft 134 and a semi-spherical shaped screw head 136. In at least one embodiment of the present invention, the screw is a cannulated screw. The shaft 134 includes a tip portion 138 and an upper end portion 140. The screw head 136 is attached to the upper end portion 140 of the shaft 134. The shaft 134 has bone engaging threads 142 provided along a length thereof. Screws in accordance with the present invention are not limited to a particular type of thread. However, double lead threads are a preferred thread for pedicle screw implements in accordance with embodiments of the present invention. With respect to single lead threads, it has been found that double lead threads allow for faster screw insertion while providing for greater pull out strength and increased fatigue strength at the bone-screw interface.

The screw head 136 is secured within the second end portion 114 of the clamping body 102. The screw head 136 is secured in a manner that limits axial displacement of the screw 104 in a direction toward the second end portion 114 of the clamping body 102, that allows pivoting of the clamping body 102 about the screw head 136 and that allows rotation of the clamping body 102 about a longitudinal axis thereof. For example, in one embodiment of the present invention, a tip portion 144 of the second end portion 114 has a mating concave contour to the semi-spherical shape of the screw head 136, thus allowing such relative rotation and pivoting between the clamping body 102 and the screw 104.

Referring to FIG. 2, the lower saddle 106 is slideably disposed within the axial passage 116 proximate the screw head 136. A screw head engaging surface 146 of the lower saddle 106 has a mating concave contour to the semi-spherical shape of the screw head 136. A spine rod engaging portion 148 of the lower saddle 106 (i.e., a generally u-shaped recess) extends above the closed end portion 120 of the spine rod receiving channel 118 when the screw head engaging surface 146 is engaged with the screw head 136. In this manner, relative movement between the screw 104 and the clamping body 102 is allowed prior to a spine rod being forcibly urged against the lower saddle by the lock screw 108 and is inhibited in response to the spine rod 133 disposed within the spine rod receiving channel 118 being forcibly urged against the lower saddle 106 by the lock screw 108 thereby causing the screw head 136 to become clamped between the tip portion 144 of the clamping body 102 and the screw head engaging surface 146 of the lower saddle 106. To further promote such inhibited relative movement, the screw head 136 can include surface texture (e.g., circumferential grooves, rough surface, etc) to enhance friction.

Figure 6:
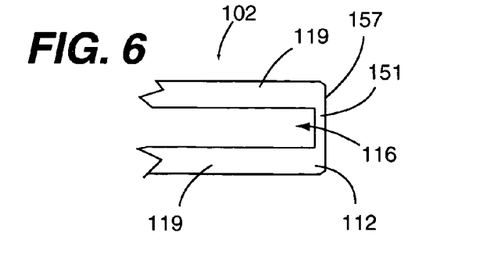
FIG. 6 is a fragmentary view showing a first alternate embodiment of the bridge member shown in FIGS. 1-3.
Figure 7:
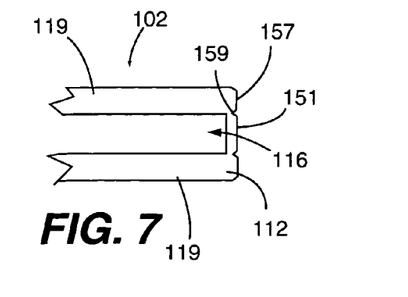
FIG. 7 is a fragmentary view showing a second alternate embodiment of the bridge member shown in FIGS. 1-3.

As shown in FIGS. 1-3 and 5, bridge members 151 are connected between the upstanding leg portions 119 at the first end portion 112 of the clamping body 102. Each one of the bridge members 151 spans across the spine rod-receiving channel 116. Preferably, but not necessarily, the bridge members 151 are annular shaped, having approximately of exactly the same interior and exterior diameters as the clamping body 102, such that the clamping body has a substantially round cross sectional shape as viewed axially from the second end portion 112. The bridge members 151 can be frangibly connected between the upstanding leg portions 119 by means such as, for example, one or more material thickness reducing relief 153 provided between each bridge member 151 and the upstanding leg portions 119 and/or an undercut slots 155 formed between the upstanding leg portions 119. Preferably, but not necessarily, a edge face of the bridge members 151 defines an end face 157 of the clamping body 102, a thickness of the upstanding leg portions 119 immediately adjacent the bridge members 151 is substantially the same as a thickness of the bridge members 151, and/or a height of the bridge members 151 (i.e., dimension along axial direction of clamping body 102) is approximately the same as the thickness thereof. Thus, the bridge members 151 need not be located in a manner in which they define the end face 157 of the clamping body 102, need not have a thickness that is substantially the same as the upstanding leg portions 119 immediately adjacent the bridge members 151, and need not have a height that is approximately the same as their thickness FIG. 6 shows an embodiment of the clamping body 102 in which the bridge members 151 are not frangibly connected between the upstanding leg portions 119, such that the upstanding leg portions 119 and the bridge members 151 jointly define the end face 157 of the clamping body 102. FIG. 7 shows an embodiment of the clamping body 102 in which the upstanding leg portions 119 and the bridge members 151 jointly define the end face 157 of the clamping body 102 and wherein notches 159 (i.e., material thickness reducing reliefs) are provided in the end face 157 of the clamping body 102 such that the bridge members 151 are frangibly connected between the upstanding leg portions 119.

Figure 8:
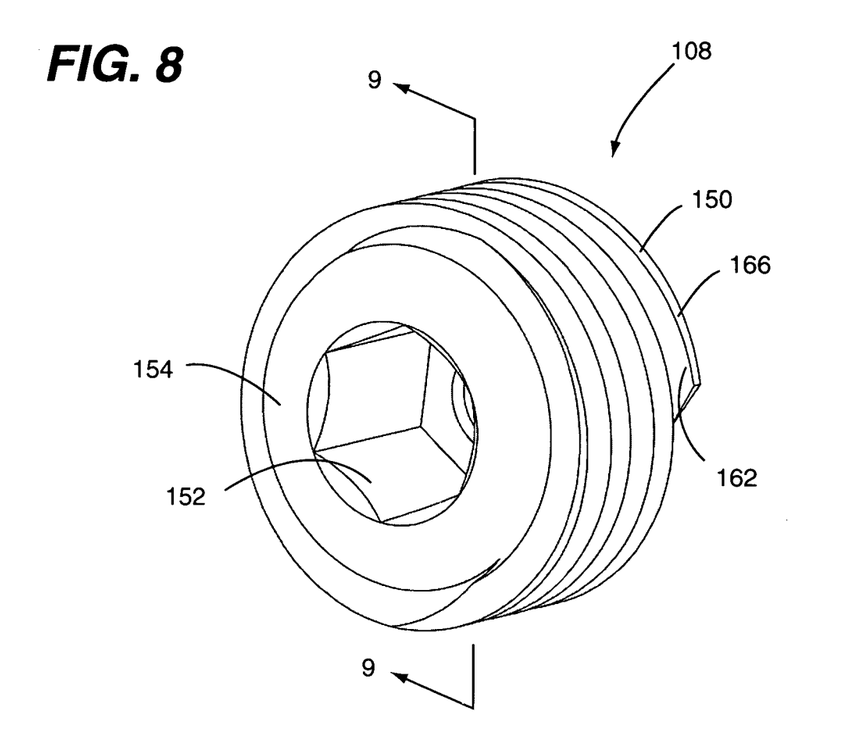
FIG. 8 is a perspective view of a locking screw assembly for a pedicle screw apparatus in accordance with an embodiment of the present invention.
Figure 9:
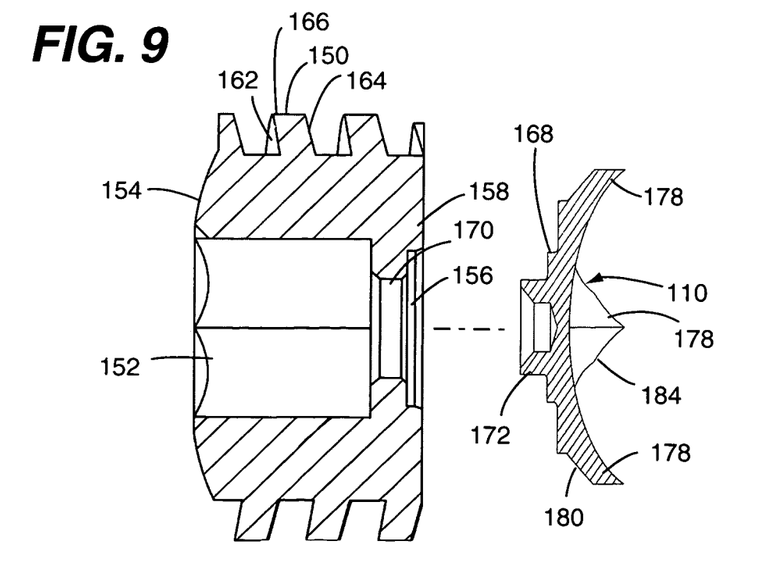
FIG. 9 is an exploded cross-sectional view taken along the line 9-9 in FIG. 8.

Referring to FIGS. 2, 8 and 9, the lock screw 108 is configured for being disposed within the axial passage 116 with threads 150 thereof matingly engaged with the clamping body threads 124. The lock screw 108 includes a fastening tool engaging structure 152 at a first end portion 154 thereof and an upper saddle receiving structure 156 at a second end portion 158 thereof. A hex socket is a preferred embodiment of the fastening tool engaging structure 152.

As best shown in FIGS. 2 and 9, the lock screw threads 150 are cupped upwardly toward the first end portion 154 of the lock screw 108. As best shown in FIG. 2, the clamping body threads 124 are cupped upwardly toward the first end portion 112 of the clamping body 102. The clamping body threads 124 include spaced apart load carrying surfaces 156, 158 and a peripheral surface 160 extending therebetween, as shown in FIG. 2. Similarly, as best shown in FIGS. 8 and 9, the lock screw threads 150 include spaced apart load carrying surfaces 162, 164 and a peripheral surface 166 extending therebetween. More specifically, with respect to the cupped thread configuration, the load carrying surfaces 156, 158 of the clamping body 102 are cupped upwardly toward the first end portion 112 of the clamping body 102 and the load carrying surfaces 162, 164 of the lock screw 108 are cupped upwardly toward the first end portion of the lock screw 108.

The cupped configuration of the lock screw threads 150 and the clamping body threads 124 advantageously enhance stability of the upstanding leg portions 119 when force is exerted thereon by the lock screw 108. Tightening of the lock screw 108 with the spine rod 133 disposed within the spine rode receiving channel 118 results in forces being exerted by the lock screw on the upstanding leg portions 119. Such force is exerted between the lock screw threads 150 and the clamping body threads 124. As such, with non-cupped threads, this force can cause the upstanding leg portions 119 to separate (i.e., splay apart), thereby leading to slipping, stripping, etc of the lock screw threads 150 with respect to the clamping body threads 124. The cupped configuration of the lock screw threads 150 and the clamping body threads 124 as disclosed herein advantageously causes the upstanding leg portions 119 to be drawn together when force is exerted on the upstanding leg portions 119 by the lock screw 108. Accordingly, a pedicle screw apparatus configured with cupped lock screw threads and the clamping body threads as disclosed herein provide for a superior interface between a clamping body and lock screw thereof and provide for superior structural robustness of upstanding leg portions thereof with the lock screw tightened in place.

Referring now to FIGS. 2, 9, 10 and 11, the upper saddle 110 is engaged at a first end portion 168 thereof with the upper saddle receiving structure 156 of the lock screw 108. The upper saddle 110 is engaged with the upper saddle receiving structure 156 in a manner allowing the upper saddle 110 to rotate about a centerline axis of the lock screw 108. As shown, in one embodiment, the upper saddle receiving structure 156 includes a passage 170 through which a mounting post 172 of the upper saddle extends, thus allowing rotation therebetween.

Figure 10:
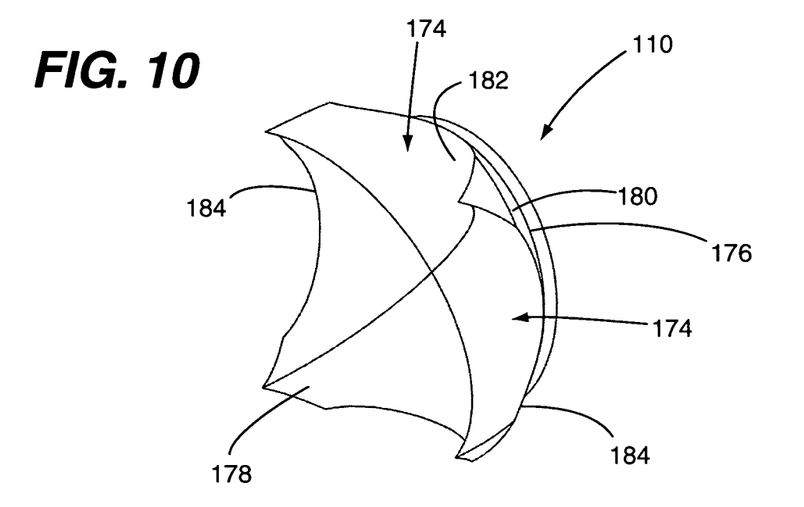
FIG. 10 is a perspective view showing a lower surface of an upper saddle for a pedicle screw apparatus in accordance with an embodiment of the present invention.

Perpendicularly intersecting spine rod receiving channels 174 extend through a spine rod engaging portion 176 of the upper saddle 110, as best shown in FIG. 10. The perpendicularly intersecting configuration of the spine rod receiving channels 174 is configured such that an outwardly-extending spine rod engaging structure 178 is provided between adjacent ones of the spine rod receiving channels 174. It is disclosed herein that one function of the spine rod engaging structure 178 is to align the upper saddle 110 to the spine rod 133. In the case where one of the spine rod receiving channels 174 is not fully aligned with a longitudinal axis of the spine rod 133, contact of the spine rod 133 by one of the spine rod engaging structure 178 causes rotation of the upper saddle 110 with respect to the spine rod 133 in response to bringing the upper saddle 110 into contact with the spine rod 133. As such, the upper saddle 110 will seek alignment (i.e., self aligning) with the spine rod 133 as the upper saddle is brought into further contact with the spine rod 133.

Figure 11:
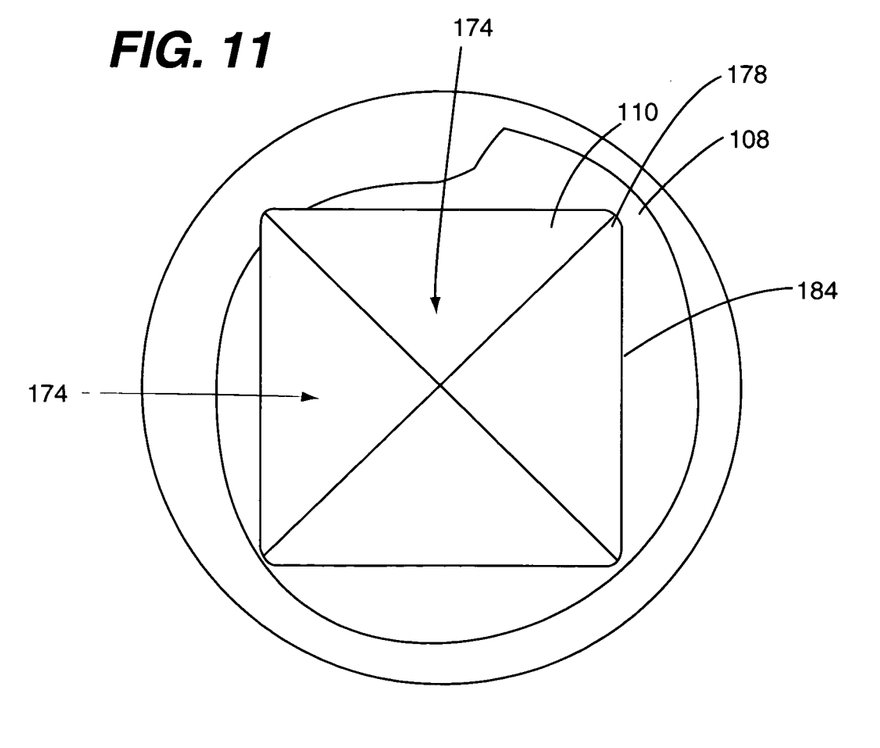
FIG. 11 is a cross sectional view taken along the line 11-11 in FIG. 10.

As best shown in FIG. 10, an upper surface 180 and a lower surface 182 of each spine rod engaging structure 178 are acutely angled with respect to each other and a channel edge 184 defined between the upper and lower surfaces 180, 182 is sharply pointed. Furthermore, the upper surface 180 of each spine rod engaging structure 178 is downwardly contoured such that a thickness of each spine rod engaging structure 178 is thinnest at a tip portion 184 thereof. The spine rod engaging portion 176 has a generally square end view profile such that the channel edge 184 defined between the upper and lower surfaces 180, 182 are generally straight in the end view (FIG. 11). The sharply pointed configuration advantageously serves to mechanically lock (i.e., engage) the upper saddle into position on a respective spine rod, thus preventing unintentional movement therebetween. Similarly, the downwardly contoured configuration of the upper surface 180 of the spine rod engaging structures 178, and the overall configuration of the upper saddle 110, serves to allow controlled deformation of the spine rod engaging structures 178. Such controlled deformation further promotes mechanically locking of the upper saddle in position on the respective spine rod (i.e., through the sharply pointed channel edge 184 biting into the surface of the spine rod), thus preventing unintentional movement therebetween.

In the preceding detailed description, reference has been made to the accompanying drawings that form a part hereof, and in which are shown by way of illustration specific embodiments in which the present invention may be practiced. These embodiments, and certain variants thereof, have been described in sufficient detail to enable those skilled in the art to practice embodiments of the present invention. It is to be understood that other suitable embodiments may be utilized and that logical, mechanical, chemical and electrical changes may be made without departing from the spirit or scope of such inventive disclosures. To avoid unnecessary detail, the description omits certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A clamping body for a pedicle screw assembly, comprising:
  a first end portion;
  a second end portion;
  an axial passage extending axially between the first and second end portions;
  a spine rod receiving channel extending between the first and second end portions of the clamping body thereby forming upstanding leg portions of the clamping body, wherein a closed end portion of the spine rod receiving channel is located at the second end portion of the clamping body and wherein each one of said upstanding leg portions has a semi-circular cross-sectional shape;
  a material thickness reducing relief provided in an outer surface of each one of said upstanding leg portions at a location between the closed end portion of the spine rod receiving channel and the first portion of the clamping body such that a segment of each one of said upstanding leg portions extending between the material thickness reducing relief and the first end portion of the clamping body is frangibly detachable from a segment of each one of said upstanding leg portions extending between the material thickness reducing relief and the closed end portion of the spine rod receiving channel; and
  a first bridge member connected between said upstanding leg portions at the first end portion of the clamping body, wherein the first bridge member spans across the spine rod receiving channel, wherein the first bridge member has a semi-circular cross-sectional shape and is substantially concentric with each one of said upstanding leg portions, wherein a first undercut slot is provided between the first bridge member and the first one of said upstanding leg portions such that the first one of said upstanding leg portions is connected to the first bridge member by a first tab of material at a closed end portion of the first undercut slot.

2. The clamping body of claim 1 wherein
a material thickness reducing relief is provided in a surface of at least one of the tabs of material for causing the first bridge member to be frangibly connected to at least one of said upstanding leg portions.

3. The clamping body of claim 1 wherein
the first bridge member and each one of said upstanding leg portions have approximately the same interior diametrical dimension.

4. The clamping body of claim 1, further comprising:
a second bridge member connected between said upstanding leg portions at the first end portion of the clamping body;
wherein a second undercut slot is provided between the second bridge member and the first one of said upstanding leg portions such the first one of said upstanding leg portions is connected to the second bridge member by the first tab of material;
wherein the second bridge member has a semi-circular cross-sectional shape and is substantially concentric with each one of said upstanding leg portions; and
wherein the first and second bridge members each span across a respective one of the spine rod receiving channels.

5. The clamping body of claim 4 wherein:
the second bridge member is substantially concentric with each one of said upstanding leg portions; and
the first and second bridge members and each one of said upstanding leg portions have approximately the same interior diametrical dimension.

6. The clamping body of claim 4 wherein each one of the bridge members is frangibly connected to at least one of said upstanding leg portions.

7. A clamping body for a pedicle screw assembly, comprising:
  a first end portion;
  a second end portion;
  an axial passage extending axially between the first and second end portions of the clamping body;
  a spine rod receiving channel extending between the first and second end portions thereby forming upstanding leg portions of the clamping body, wherein a closed end portion of the spine rod receiving channel is located at the second end portion of the clamping body;

a material thickness reducing relief provided in an outer surface of each one of said upstanding leg portions at a location between the closed end portion of the spine rod receiving channel and the first end portion of the clamping body such that a segment of each one of said upstanding leg portions extending between the material thickness reducing relief and the first end portion of the clamping body is frangibly detachable from a segment of each one of said upstanding leg portions extending between the material thickness reducing relief and the closed end portion of the spine rod receiving channel; and a bridge member connected between said upstanding leg portions at the first end portion of the clamping body, wherein the bridge member spans across the spine rod receiving channel, wherein the bridge member is an annularly shaped ring, wherein each one of said upstanding leg portions has a semi-circular cross-sectional shape, wherein the bridge member is substantially concentric with each one of said upstanding leg portions, wherein an undercut slot is provided between the bridge member and each one of said upstanding leg portions such the first one of said upstanding leg portions is connected to the bridge member by a first tab of material extending between first adjacent end portions of said undercut slots and the second one of said upstanding leg portions is connected to the bridge member by a second tab of material extending between second adjacent end portions of said undercut slots, wherein each one of said tabs of material has a material thickness reducing relief in a surface thereof.

8. A clamping body for a pedicle screw assembly, comprising:

a first end portion;

a second end portion;

an axial passage extending axially between the first and second end portions of the clamping body;

a spine rod receiving channel extending between the first and second end portions thereby forming upstanding leg portions of the clamping body, wherein a closed end portion of the spine rod receiving channel is located at the second end portion of the clamping body;

a material thickness reducing relief provided in an outer surface of each one of said upstanding leg portions at a location between the closed end portion of the spine rod receiving channel and the first end portion of the clamping body such that a segment of each one of said upstanding leg portions extending between the material thickness reducing relief and the first end portion of the clamping body is frangibly detachable from a segment of each one of said upstanding leg portions extending between the material thickness reducing relief and the closed end portion of the spine rod receiving channel; and a bridge member connected between said upstanding leg portions at the first end portion of the clamping body, wherein the bridge member spans across the spine rod receiving channel, wherein the bridge member is annularly shaped, wherein each one of said upstanding leg portions has a semi-circular cross-sectional shape, wherein the bridge member is substantially concentric with each one of said upstanding leg portions, wherein the bridge member and each one of said upstanding leg portions have approximately the same interior and exterior diametrical dimensions at regions where the bridge member is connected to each one of said upstanding leg portions, wherein a material thickness reducing relief is provided between the bridge member and a first one of said upstanding leg portions for causing the bridge member to be frangibly connected to the first one of said upstanding leg portions, wherein the material thickness reducing relief between the bridge member and the first one of said upstanding leg portions is positioned between opposing undercut slots, wherein a first one of the undercut slots extends from a first edge of the first one of said upstanding leg portions, and wherein a second one of the undercut slots extends from a second edge of the first one of said upstanding leg portions.

9. The clamping body of claim 8 wherein the material thickness reducing relief between the bridge member and the first one of said upstanding leg portions extends horizontally between a closed end of each one of the undercut slots.

10. The clamping body of claim 9 wherein the material thickness reducing relief intersects an edge portion of at least one of the undercut slots.

11. The clamping body of claim 8 wherein the material thickness reducing relief intersects an edge portion of at least one of the undercut slots.

* * * * *